United States Patent [19]

Bryant et al.

[11] Patent Number: 4,710,587

[45] Date of Patent: Dec. 1, 1987

[54] PROCESS FOR REMOVING TRIORGANOPHOSPHINE FROM AN ORGANIC LIQUID

[75] Inventors: David R. Bryant; Richard A. Galley, both of South Charleston, W. Va.

[73] Assignees: Union Carbide Corporation, Danbury, Conn.

[21] Appl. No.: 762,028

[22] Filed: Aug. 2, 1985

Related U.S. Application Data

[63] Continuation of Ser. No. 140,740, Apr. 16, 1980, abandoned.

[51] Int. Cl.$^4$ .............................................. C07C 45/80
[52] U.S. Cl. ........................................ 568/454; 568/8; 568/17; 568/455; 568/456; 568/882; 568/909
[58] Field of Search .................. 568/17, 8, 454, 455, 568/456, 882, 909; 252/413, 431 B

[56] References Cited

U.S. PATENT DOCUMENTS

| | | |
|---|---|---|
| 3,527,809 | 9/1970 | Pruett et al. ........................ 260/604 |
| 3,968,134 | 7/1976 | Gregorio et al. ..................... 568/17 |
| 4,072,628 | 2/1978 | Kruse et al. ........................ 252/415 |
| 4,113,754 | 9/1978 | Kummer et al. ..................... 568/454 |
| 4,148,830 | 4/1979 | Pruett et al. ....................... 568/454 |
| 4,242,284 | 12/1984 | Harris et al. ........................ 568/454 |
| 4,247,486 | 1/1981 | Brewester et al. ................... 568/454 |
| 4,260,828 | 4/1981 | Morrell et al. ...................... 568/454 |
| 4,283,304 | 8/1981 | Bryant et al. ....................... 252/413 |
| 4,297,239 | 10/1981 | Bryant et al. ....................... 252/412 |

FOREIGN PATENT DOCUMENTS

| | | |
|---|---|---|
| 7768 | 2/1980 | European Pat. Off. . |
| 86301 | 8/1974 | Japan . |
| 117402 | 9/1974 | Japan .................... 568/17 |

*Primary Examiner*—Glennon H. Hollrah
*Assistant Examiner*—Raymond Covington
*Attorney, Agent, or Firm*—R.J. Finnegan

[57] ABSTRACT

A process for selectively removing alkyl substituted phosphine from an organic liquid containing same and triarylphosphine by treating said liquid with phosphoric acid.

8 Claims, No Drawings

1

PROCESS FOR REMOVING TRIORGANOPHOSPHINE FROM AN ORGANIC LIQUID

This application is a continuation of prior U.S. application Ser. No. 140,740 filed 4/16/80 now abandoned.

FIELD OF THE INVENTION

This invention relates to a process for removing triorganophosphine from an organic liquid containing alkyl substituted phosphine and triarylphosphine by treating said liquid with phosphoric acid. More particularly this invention is directed to a process for selectively removing alkyl substituted phosphine from said liquid.

BACKGROUND OF THE INVENTION

Processes for forming an aldehyde by the reaction of an olefin with carbon monoxide and hydrogen in the presence of a rhodium-triarylphosphine complex catalyst in the presence of an excess of free triarylphosphine ligand to produce aldehydes rich in the normal isomer are well known in the art as seen for example by U.S. Pat. No. 3,527,809 and Belgium Patent No. 853,377. It is also known that, under hydroformylation conditions, some of the product aldehydes may condense to form by-product, high boiling aldehyde condensation products such as aldehyde dimers and trimers which may serve as solvents for the hydroformylation process as seen for example by U.S. Pat. No. 4,148,830. It has further been observed that the presence of alkyldiarylphosphine (such as propyldiphenylphosphine or ethyldiphenylphosphine) in the rhodium-catalyzed hydroformylation of propylene inhibits catalyst productivity and that when triarylphosphine ligand is employed in the hydroformylation of an alpha-olefin, alkyldiarylphosphine is produced in situ, the "alkyl" group thereof being derived from the alpha-olefin undergoing hydroformylation and the "aryl" groups thereof being the same as the aryl of the triarylphosphine. While Belgium patent No. 863,267 teaches that the presence of such alkyldiarylphosphine can be compensated for by controlling the hydroformylation conditions of the process, the continued build-up of alkyl substituted phosphine over a period of time in a continuous hydroformylation process to produce aldehydes rich in the normal isomer will eventually lead to an unacceptable decrease in the rate of reaction and activity of the rhodium complex catalyst due to the affinity of said alkyl substituted phosphine for the rhodium catalyst.

More recently U.S. application Ser. Nos. 40,913 and 108,279 filed May 21, 1979 and Dec. 28, 1979 respectively, now U.S. Pat. No. 4,283,304, disclose removing triorganophosphine from a composition containing a rhodium complex hydroformylation catalyst or concentrate of said composition by treating said composition or concentrate with an alpha, beta-unsaturated compound or anhydride thereof, such as maleic acid or maleic anhydride. The process is particularly useful for selectively removing alkyl substituted phosphine from said compositions in order to rejuvenate the activity of the rhodium complex catalyst.

However, even after enhancing the activity of the rhodium complex catalyst by removal of alkyl substituted phosphine from the hydroformylation reaction medium, eventually the rhodium complex catalyst will become spent (that is to say such enhancing procedures cannot be repeated indefinitely since eventually the activity of the catalyst will have decreased to such a point that it is no longer economically desirable to operate the hydroformylation process) and the catalyst will have to be replaced. Moreover, improper procedures and/or contaminates, and the like at the initial start-up of a hydroformylation process could result in the early formation of an undesirable hydroformylation medium that must also be replaced.

Upon such occurrences it becomes important to recover the rhodium values of the complex catalyst due to the inordinately high cost of rhodium. Such recovery methods will obviously entail the removal and/or destruction of the organic compounds of the hydroformylation composition, and such poses the problem of what to do with the large excess of triarylphosphine that must be removed from the catalyst solution. For example U.S. application Ser. Nos. 58,123 abandoned and now U.S. Pat. Nos. 4,097,239 and 120,101 filed July 16, 1979 and Feb. 28, 1980 respectively, (the entire disclosures of which are incorporated herein by reference thereto) disclose methods for concentrating a spent hydroformylation medium containing a rhodium complex catalyst via distillation to produce a rhodium complex concentrate which can serve as the source of reactivated rhodium for a rhodium complex hydroformylation process. Such methods result in an organic liquid distillate containing alkyl substituted phosphine and a large excess of triarylphosphine. Accordingly methods which allow for the selective removal of alkyl substituted phosphine from an organic liquid containing alkyl substituted phosphine and triarylphosphine can be clearly beneficial to the state of the art since they can provide an excellent means for rejuvenating the activity of a spent rhodium complex catalyst or for recovering and obtaining large amounts of previously used triarylphosphine for reuse in a hydroformylation process.

SUMMARY OF THE INVENTION

It has now been discovered that alkyl substituted phosphine can be selectively removed from an organic liquid containing alkyl substituted phosphine and triarylphosphine by treatment with phosphoric acid.

Thus it is an object of this invention to provide a process for selectively removing alkyl substituted phosphine from an organic liquid containing alkyl substituted phosphine and triarylphosphine by treating said liquid with phosphoric acid. Other objects and advantages of this invention will become readily apparent from the following description and appended claims.

Accordingly the generic aspect of this invention can be described as a process for selectively removing alkyl substituted phosphine of the formula

wherein R is an alkyl radical, R' is an alkyl or aryl radical and R" is an aryl radical from an organic liquid, said process comprising (1) mixing an organic liquid containing triarylphosphine and alkyl substituted phosphine of formula (I) above with an aqueous solution of 40 to 60 percent by weight phosphoric acid ($H_3PO_4$);

(2) allowing the aqueous mixture of said step (1) to settle into two distinct liquid phases, and (3) separating the aqueous-acid phase which contains the solubilized protonated reaction product of the alkyl substituted phosphine with said phosphoric acid from the non-aqueous, organic phase resulting from said steps (1) and (2) and wherein the volume ratio of the said aqueous phosphoric acid solution employed to the volume of said organic liquid employed is at least about 0.1 to 1.

DESCRIPTION OF THE PREFERRED EMBODIMENTS

The organic liquids from which the alkyl substituted phosphine may be removed by the present invention may be any organic liquid not miscible with water containing an alkyl substituted phosphine of formula (I) above and a triarylphosphine which is free from contaminants that would adversely affect the basic purpose of the present invention. Preferably said organic liquids are derived by distilling a hydroformylation reaction medium or derivative thereof containing both types of said phosphines, such as disclosed in the prior art discussed above, to form a distillate containing both types of said phosphines, the remainder of said distillate consisting essentially of the solvent and/or higher boiling aldehyde condensation by-products of said hydroformylation reaction medium. Thus it should be clear that the particular distillation procedure for producing such organic liquid distillates is not a critical feature of the present invention since such serves only as a means for furnishing the organic liquid employed as a starting material of the present invention. In general, however, the preferred organic liquids employed in the present invention are those distillates containing an alkyl substituted phosphine of formula (I) above and a triarylphosphine obtained according to the distillation and concentration procedures outlined in said U.S. application Ser. Nos. 58,123 and 120,101.

The triarylphosphine present in the organic liquids used in this invention can of course be any triarylphosphine suitable for use in any hydroformylation reaction such as those triarylphosphines and reactions taught by the prior art discussed above. Illustrative triaylphosphines are lriphenylphospine, trinaphthylphosphine, tritolylphospine, tri(p-biphenyl) phosphines, tri-(p-methoyphenyl) phosphine, p-(N, N-dimethylamino)-phenyldiphenylphosphine, and the like. Triphenylphosphine is presently the preferred triarylphosphine ligand.

The alkyl substituted phosphine present in the organic liquid used in this invention can be any phosphine that is more basic than the triarylphosphine in said composition. For example, propyldiphenylphosphine is more basic (pKa=about 4.5 to 5.5) than triphenylphosphine (pKa=2.73). Illustrative examples of such alkyl substituted phosphines include those encompassed by Formula (I) above. Moreover, as explained above, such alkyl substituted phosphines are normally derived from the particular olefin that is hydroformylated and the particular triarylphosphine employed in said hydroformylation process. For example, the hydroformylation of propylene by the preferred procedure described in Belgium Patent No. 853,377 leads to the in situ formation of propyldiphenylphosphine as well as some detectable butyldiphenylphosphine. Dialkylarylphosphines which may be present as a result of in situ formation or deliberate addition to a hydroformylation process are more basic than the triarylphosphine and can also be removed by the process of this invention.

Accordingly, the alkyl radical of said alkyl substituted phosphine may be any alkyl radical containing 2 to 20, preferably 2 to 10, carbon atoms. They may be straight or branched-chain and may contain groups or substituents which do not essentially interfere with the course of the process of this invention, such as hydroxyl and alkoxy radicals, and the like. Illustrative of such alkyl radicals include ethyl, propyl, isopropyl, butyl, pentyl, hexyl, heptyl, octyl, decyl, dodecyl, octadecyl, 2-ethyl-hexyl, eicosyl, 3-phenyl-propyl, 3-hydroxypropyl, 4-hydroxyhexyl, 4-hydroxyoctyl, 2-ethoxyethyl, 2-methoxyethyl, 3-ethoxypropyl, and the like.

Moreover, since it is generally preferred to hydroformylate alpha-olefins containing 2 to 5 carbon atoms the more preferred alkyl radicals of said alkyl substituted phosphines are ethyl, propyl, butyl and pentyl. Likewise, the aryl radical of said alkyl substituted phosphines may correspond to the aryl group of the triarylphosphine ligand employed in the hydroformylation processes as discussed above, the preferred aryl radical being a phenyl radical derived from triphenylphosphine. The most preferred alkyl substituted phosphines are ethyldiphenylphosphine, propyldiphenylphosphine and butyldiphenylphosphine, especially propyldiphenylphosphine. Note, however, that it is not applicants' intention to be bound by any precise discussion or explanation of how said alkyl substituted phosphines are formed in situ, it being sufficient for the purpose of this invention to simply point out that their in situ formation is possible and that such alkyl substituted phosphines can be selectively removed when present in the organic liquids employed.

The various amounts of triarylphosphine and said alkyl substituted phosphine contained in the organic liquids employed in this invention are not critical since the subject invention is directed to selectively removing all or any portion of said alkyl substituted phosphine in the organic liquid. Moreover, since the preferred organic liquids of this invention correspond to the liquid distillates derived from concentrating a hydroformylation medium or derivative thereof as discussed above, the amounts of said triarylphosphine and alkyl substituted phosphine will preferably correspond to those amounts of said phosphines found in the spent hydroformylation mediums from whence said distillates are derived. Thus in general the amount of alkyl substituted phosphine present in the organic liquids employable in this invention may range from 0.1 to about 5 percent by weight based on the total weight of the organic liquid, while the amount of triarylphosphine present in said organic liquid may vary from about 1 percent to about 25 percent by weight higher, based on the total weight of the organic liquid. It is further preferred that the organic liquid of this invention contain at least 0.5 percent by weight of alkyl substituted phosphine based on the total weight of the organic liquid, while the amount of triarylphosphine present is at least twice as much as that of said alkyl substituted phosphine.

It is of course, also to be understood that since said hydroformylation reactions are normally conducted in the presence of a solvent for the catalyst, the organic liquids employed in this invention can also encompass the presence of such solvents in similar amounts. Such solvents are well known in the art and encompass those described in U.S. Pat. No. 3,527,809 and more preferably the higher boiling liquid aldehyde condensation products which are more fully described in U.S. Pat. No. 4,148,830. Such condensation products can be preformed or produced in situ during hydroformylation and include the complex mixture of high boiling liquid products of the hydroformylation processes described above. Accordingly, the amount of solvent and/or amount of higher boiling aldehyde condensation products present in the organic liquid starting material of this invention may range from about 70 to about 98.9 parts by weight based on the total weight of the liquid composition. Of course it is to be understood that the organic liquids of this invention can also encompass the possible presence of minor amounts of other ingredients such as phosphine oxides and the like.

As pointed out above, the preferred organic liquids employed in this invention are those liquids derived from distilling a spent hydroformylation reaction medium or derivative thereof containing both types of said phosphines to form a distillate consisting essentially of alkyl substituted phosphine, triarylphosphine and the solvent and/or higher boiling aldehyde condensation by-products of said hydroformylation medium. Moreover the preferred distillation procedure which may be employed to prepare such organic liquid distillates can be found more fully discussed in said U.S. application, Ser. Nos. 58,123 and 120,101. Such a distillation procedure preferably takes place in two stages, the first stage being conducted at temperatures of about 20° to 250° C., preferably from 20° to 190° C., and pressures of about 1000 to about 0.1 mm Hg., preferably about 150 to 0.5 mm Hg; the second stage of the distillation being conducted at temperatures of about 25° to 350° C., preferably from about 150° to about 350° C. and pressures of about 100 to $1 \times 10^{-6}$ mm Hg., preferably about 20 to 0.1 mm Hg. so as to further concentrate the bottom or residue product of the first stage to the desired rhodium concentrate.

The first distillation stage is employed to distill off and remove the most volatile components, e.g. the aldehyde products, that are present in the spent hydroformylation medium since such low boiling volatile components interfere with obtaining the desired low pressures employed in the second distillation stage and needed for the most effective removal of the less volatile (i.e. higher boiling) components. Of course it is obvious that the most volatile components (e.g. the aldehyde products) so removed may be recovered from said distillate stream in any conventional manner or discarded as desired.

The second distillation stage involves taking the liquid residue or bottoms of said first distillation stage containing the partially deactivated rhodium complex catalyst and less volatile components, such as the solvent and phosphine ligands, of the spent hydroformylation reaction medium and subjecting it to further distillation at the reduced pressures given above so as to distill off and remove said remaining high boiling volatile materials. It is the distillate of said second stage distillation that is the most preferred organic liquid employable in this invention. Of course it is understood that since said second distillation stage may be carried out more than once if desired, the organic liquid employable in this invention can comprise a composite of the distillates of such successive distillations. Moreover, the distillation of each separation stage can be carried out by using any suitable distillation system and can take place on a continuous and/or discontinuous (batch) basis. In general it is preferred to carry out both distillation stages in a thin-film evaporator, such as a wiped-film or falling film evaporator with the second distillation stage being carried out under a high vacuum. Such evaporators are well known in the art and thus need not be further discussed herein.

As pointed out above, an aqueous solution of 40 to 60 percent by weight phosphoric acid can be employed herein to selectively remove the alkyl substituted phosphine from the organic liquid starting materials of this invention.

The process of this invention comprises mixing the organic liquid starting material as defined above with the aqueous solution of phosphoric acid, allowing the mixture thereof to settle into two distinct phases and separating the aqueous-acidic (bottom) phase which contains the solubilized products of both alkyl substituted phosphine and triarylphosphine from the organic liquid, i.e. non-aqueous, top phase containing the unreacted triarylphosphine and remainder of the organic liquid starting material.

The process of this invention may be described as one in which the phosphine compounds of the organic liquid react with the phosphoric acid in the presence of water to form a water soluble protonated phosphine. Furthermore, while it is not intended to limit the present invention by the above explanation as to the precise order of reaction involved, it has been found that alkyl substituted phosphines are more basic than triarylphosphines and thus more reactive towards phosphoric acid than triarylphosphine. This difference in basicity provides the basis for the selective removal of the alkyl substituted phosphine. Furthermore, it is not intended to be bound by any discussion of the particular structure of the solubilized protonated reaction product, since it is sufficient for the purpose of the present invention to provide a means for selectively removing the alkyl substituted phosphine.

The reaction of the process of this invention is exothermic and can be carried out at any suitable temperature. Moreover, the process can be carried out at sub-atmospheric, atmospheric, or elevated pressures, as desired. In general, the temperature may range from about 0° C. to about 150° C. Temperatures of 100° C. and above, of course, require elevated pressures. Preferably, the process is performed at about atmospheric pressure and at less than 100° C., the more preferred temperature being from about 25° C. to about 80° C. It is important to thoroughly mix the reactants involved, and such can be effected by any conventional means such as stirring and the like. The general reaction is quite rapid and will normally be completed within an hour and more preferably within one-half hour depending on the reactants, temperature and efficiency of mixing involved.

Sincerely process of this invention is designed for the selective removal of alkyl substituted phosphine and not triarylphosphine from the organic liquid starting material, an aqueous solution of about 40 to about 60% by wt. of phosphoric acid should be employed. The amount of said aqueous acid solution employed in the process of this invention is not narrowly critical and need only be that amount which is sufficient to solubilize that amount of the protonate reaction products of said phosphines and said phosphoric acid resulting from the process of this invention. However, the amount of water employed should not be so great so as to provide an aqueous solution of less than about 40 percent by weight phosphoric acid, since at such concentrations very little alkyl substituted phosphine may be extracted. Nor should the amount of water be so little as to provide an aqueous solution of more than about 60 percent by weight phosphoric acid, since at such concentrations the simultaneous extraction of triarylphosphine may become intolerably high. Of course it is obvious that some triarylphosphine may be and undoubtedly is also removed from the organic liquid starting material in the same manner as described above (i.e. as a solubilized protonated reaction product with the phosphoric acid). However, the process of this invention is designed to remove as much alkyl substituted phosphine as possible from the starting organic liquid while at the same time removing very little of the triarylphosphine from said liquid.

While, at least about 0.1 volume equivalents of said aqueous phosphoric acid solution based on the amount of organic liquid starting material to be treated can be used, in general, it is preferred to employ an equal volume of said aqueous acid solution.

Moreover, the process of this invention is preferably carried out under an inert atmosphere, such as nitrogen, in order to avoid excess loss of the triarylphsophine by oxidation to triarylphosphine oxide.

Upon completion of the phosphine-phosphoric acid reaction of the process of this invention, the mixture is allowed to settle into two distinct liquid phases, the bottom phase being the aqueous-acidic phase containing the solubilized protonated reaction products of said triorganophosphines with said phosphoric acid, which can be separated from the organic (i.e., non-aqueous, top) liquid phase which contains unreacted organic liquid by any suitable method, such as by draining off the bottom layer or decanting off the top layer, and the like.

The subject process is unique in that the alkyl substituted phosphine and triarylphosphine extracted by the phosphoric acid in the aqueous-acidic phase can be recovered if desired by neutralizing said phase with any suitable base e.g. potassium hydroxide and the free phosphine extracted into any suitable organic solvent, e.g. ethyl ether. Aternatively, alkyl substituted phosphine can be recovered from the aqueous-acidic phase by diluting it with sufficient water to such an extent that the phosphoric acid is no longer strong enough to protonate the alkyl substituted phosphine and said phosphine separates out. The free alkyl substituted phosphine can then be extracted into any suitable organic solvent as described above, or collected by filtration.

More particularly, the process of this invention is especially beneficial in the hydroformylation field, since it provides for the selective removal of alkyl substituted phosphine from a distillate also containing a large amount of triarylphosphine, the remainder of the distillate consisting essentially of a hydroformylation solvent and/or the higher boiling aldehyde condensation products of a hydroformylation medium as described above. Thus the process of this invention provides a unique method for providing large amounts of triarylphosphine suitable for reuse in a hydroformylation process. However it is recommended for commercial operations, that the organic (non-aqueous) liquid phase containing the unreacted triarylphophine obtained by the process of this invention be thoroughly washed with any suitable aqueous alkaline solution such as a sodium bicarbonate solution to remove any phosphoric acid that might be present, and after the alkaline solution is removed, further washed with water several times to remove any amount of the basic compound employed in the initial wash, prior to reusing said triarylphosphine in a hydroformylation process.

The following examples are illustrative of the present invention and are not to be regarded as limitative. It is to be understood that all of the parts, percentages and proportions referred to herein and in the appended claims are by weight unless otherwise indicated.

EXAMPLE 1

A variety of acids of similar strengths were used to treat solution mixtures of 1.8 area % propyldiphenylphosphine and 9.6 area % triphenylphosphine in Texanol ®, a mixture of butyraldehyde trimers. In each case the solution mixture was stirred with an equal volume of an aqueous solution of the acid employed at room temperature and under nitrogen for about 30 minutes. The treated mixtures were then allowed to settle into two distinct liquid phase layers and the phases were separated. The organic (non-aqueous) layer was analyzed for phosphine and the results are given in Table I below.

TABLE I

| Acid | Propyldiphenyl-phosphine (Area %) | Triphenyl-phosphine (Area %) |
| --- | --- | --- |
| 40% $H_3PO_4$ | 1.52[a] | 9.29[a] |
| 40% Formic | 1.51[a] | 7.75[a] |
| 10% Oxalic | 1.54[a] | 8.20[a] |
| 40% Citric | 1.59[a] | 8.23[a] |
| 50% Phosphorous | 0.48[a] | 8.42[a] |
| 60% $H_3PO_4$ | 0.11[b] | 9.21[b] |

[a]Average of four determinations.
[b]One determination.

EXAMPLE 2

A solution mixture of propyldiphenylphosphine (1.8 area %) and triphenylphosphine (9.2 area %) in Texanol ®, a mixture of butyraldehyde trimers was stirred with an equal volume of an aqueous solution of 60% phosphoric acid at room temperature under nitrogen for thirty minutes and allowed to settle into two distinct liquid layers. The phases were separated and the organic (non-aqueous) layer analyzed for phosphine. The same procedure was repeated, except that this time the solution mixture was stirred under air. The results are given in Table II below.

TABLE II

| Atmosphere | Propyldiphenyl-phosphine (area %) | Triphenyl-phosphine (area %) |
| --- | --- | --- |
| Nitrogen | 0.11 | 9.2 |
| Air | 0.08 | 8.0 |

EXAMPLE 3

A series of solutions containing various concentrations of propyldiphenylphosphine in concentrated phosphoric acid (about 85 weight %) were titrated with water at room temperature to the turbidity endpoint. The weight percent of the three components were calculated and are given in Table III below. All Final concentrations are an average of three determinations.

TABLE III

| Solution | Propyldiphenyl-phosphine (wt. %) | wt. % $H_3PO_4$ | wt. % $H_2O$ |
| --- | --- | --- | --- |
| Initial | 1.0 | 84.2 | 14.8 |
| Final | 0.4 | 35.6 | 63.9 |
| Initial | 5.0 | 80.7 | 14.3 |
| Final | 2.5 | 40.9 | 56.6 |
| Initial | 10.0 | 76.5 | 13.5 |
| Final | 5.2 | 40.3 | 54.4 |
| Initial | 20.0 | 68.0 | 12.0 |

TABLE III-continued

| Solution | Propyldiphenyl-phosphine (wt. %) | wt. % H$_3$PO$_4$ | wt. % H$_2$O |
| --- | --- | --- | --- |
| Final | 12.8 | 43.7 | 43.5 |
| Initial | 30.0 | 59.5 | 10.5 |
| Final | 24.0 | 47.6 | 28.4 |

A three phase diagram constructed from this data indicates that for the propyldiphenylphosphine range studied, turbidity begins at 36–47% phosphoric acid concentrstion.

EXAMPLE 4

Example 4 was repeated using triphenylphosphine instead of propyldiphenylphosphine. The weight percent of the three components were calculated and are given in Table IV below. All final concentrations are an average of three determinations.

TABLE IV

| Solution | Triphenyl-phosphine (wt. %) | wt. % H$_3$PO$_4$ | wt. % H$_2$O |
| --- | --- | --- | --- |
| Initial | 1.0 | 84.1 | 14.9 |
| Final | 0.7 | 62.4 | 36.9 |
| Initial | 4.0 | 81.6 | 14.4 |
| Final | 3.3 | 66.8 | 29.9 |
| Initial | 5.0 | 80.7 | 14.3 |
| Final | 4.1 | 65.6 | 30.3 |
| Initial | 10.0 | 76.5 | 13.5 |
| Final | 8.9 | 68.6 | 22.5 |

This data indicates that for the concentration range studied, triphenylphosphine precipitation occurred in the 62–69% phosphoric acid range.

EXAMPLE 5

A solution mixture containing 2.2 area % propyldiphenylphosphine and 9.6 area % triphenylphosphine in Texanol ®, a mixture of butyraldehyde trimers was stirred under nitrogen at about 25° C. with an equal volume of an aqueous solution of 60% phosphoric acid for about thirty minutes. The mixture was allowed to settle into two distinct liquid phase layers. The phases were separated and the organic (non-aqueous) layer was analyzed and found to contain 0.08 area % propyldiphenylphosphine and 8.2 area % triphenylphosphine. The aqueous-acidic layer was diluted with water and the phosphine contained therein extracted with methylene chloride. The methylene chloride extract was analyzed by gas chromatography and found to contain more than 99% of the propyldiphenylphosphine extracted from the original solution mixture.

EXAMPLE 6

A hydroformylation reaction medium comprising a rhodium complex catalyst, propyldiphenylphosphine, triphenylphosphine and high boiling aldehyde condensation by-products was passed through an Arthur F. Smith wiped film evaporator operated at 230° to 240° C. and 0.3 to 0.5 mm Hg. at a rate of about 3 grams per minute to obtain a distillate containing propyldiphenylphosphine and triphenylphosphine, the remainder of the distillate consisting essentially of high boiling aldehyde condensation by-products. A 50 ml. sample of said distillate containing 6.7 grams of triphenylphosphine and 0.46 grams of propyldiphenylphosphine was stirred with a 50 ml. aqueous solution of 42% phosphoric acid at 30° C. for 35 minutes and the mixture allowed to settle into two distinct liquid phase layers. The phases were separated and the organic (non-aqueous) layer was analyzed for phosphine and found to contain about 0.14 grams of propyldiphenylphosphine and about 6.7 grams of triphenylphosphine. The aqueous-acidic layer was neutralized with potassium hydroxide and the phosphine contained therein extracted with ethyl ether. The ether extract was found to contain propyldiphenylphosphine and triphenylphosphine in an 8:1 ratio.

EXAMPLE 7

A hydroformylation reaction medium comprising a rhodium complex catalyst, propyldiphenylphosphine, triphenylphosphine and high boiling aldehyde condensation by-products was passed through an Arthur F. Smith wiped film evaporator to obtain a distillate containing about 319 grams of triphenylphosphine, about 21.7 grams of propyldiphenylphosphine and nil rhodium, the remainder of the distillate consisting essentially of high boiling aldehyde condensation by-products. A portion of said distillate was thoroughly mixed with an aqueous solution of 40% phosphoric acid at room temperature and the mixture allowed to separate into two distinct liquid phase layers. The phases were separated and the organic (non-aqueous) layer was washed with an aqueous solution of 10% sodium bicarbonate and then with water. After removal of the water said washed organic liquid was diluted with Texanol ®, a mixture of butyraldehyde trimers, to give an organic solution containing about 4.8 wt. % triphenylphosphine. A rhodium complex compound was then added to the solution to give a rhodium concentration of about 300 ppm and a fifteen ml. aliquot of this solution was charged to a stirred autoclave and heated to 100° C. under nitrogen. The nitrogen was discharged and the reactor charged with propylene, carbon monoxide and hydrogen in a 1:1:1 mole ratio to a pressure of about 80 psig and the propylene hydroformylated to produce butyraldehyde. The propylene hydroformylation reaction rate was 0.996 gram moles per liter hour.

Under identical conditions but without prior treatment with phosphoric acid, sodium bicarbonate and water the hydroformylation rate using said untreated distillate to form the hydroformylation medium in the same manner as described above was about 0.585 gram moles per liter hour. Base washing alone of said distillate had little effect on the hydroformylation reaction rate. Moreover a fresh rhodium catalyst hydroformylation solution prepared with new triphenylphosphine gave a rate of hydroformylation of propylene of 1.06 gram moles per liter hour under identical conditions.

EXAMPLE 8

Distillate samples containing about 2.0 wt.% propyldiphenylphosphine, about 22.4 wt.% triphenylphosphine and nil rhodium, the remainder consisting essentially of high boiling aldehyde condensation by-products obtained by distilling a rhodium complex catalyst hydroformylation medium in a wiped-film evaporator were mixed with an equal volume of an aqueous solutions of different strengths of either phosphoric acid or sufuric acid at room temperature for about 25–30 minutes. The treated mixtures were then allowed to settle into two distinct liquid phase layers and the phases were separated. The organic (non-aqueous) layer was analyzed for phosphine and the results are given in Table V below.

TABLE V

| Acid | Propyldiphenyl-phosphine (wt. %) | Triphenyl-phosphine (wt. %) |
|---|---|---|
| 30% H$_3$PO$_4$ | 1.7 | 21.2 |
| 53% H$_3$PO$_4$ | 0.7 | 20.0 |
| 72% H$_3$PO$_4$ | nil | 10.3 |
| 5% H$_2$SO$_4$ | 1.8 | 18.9 |
| 10% H$_2$SO$_4$ | 1.7 | 17.8 |
| 31% H$_2$SO$_4$ | nil | 18.3 |
| 55% H$_2$SO$_4$ | nil | 0.6 |

EXAMPLE 9

Aliquots (100 ml.) of a rhodium complex lyst hydroformylation medium that was batched distilled to remove aldehyde were analyzed and found to contain about 488 ppm rhodium, about 0.85 wt.% propyldiphenylphosphine and about 14.6 wt.% triphenylphosphine. Said aliquots were stirred with 100 ml. aqueous aliquots of 20, 40, 60, and 80 wt.% phosphoric acid at 25° C. Samples taken after various contact times were allowed to settle into two distinct liquid phase layers and the phases separated. The organic (non-aqueous) layer was analyzed for phosphine and rhodium while the aqueous-acidic layer was analyzed only for rhodium. The results are given in Table VI below.

TABLE VI

| H$_3$PO$_4$ Wt % | Fraction Layer | Contact Time (Hrs) | Propyldiphenyl Phosphine (wt %) | Triphenyl-phosphine (Wt %) | Rhodium (ppm) |
|---|---|---|---|---|---|
| 20 | organic | 0.5 | 0.95 | 14.5 | 412 |
| 20 | organic | 2.0 | 0.80 | 13.4 | 406 |
| 20 | organic | 3.0 | 0.62 | 13.4 | a |
| 20 | organic | 4.0 | 1.05 | 14.8 | 401 |
| 20 | aqueous | 0.5 | | | 11 |
| 20 | aqueous | 2.0 | | | 15 |
| 20 | aqueous | 3.0 | | | a |
| 20 | aqueous | 4.0 | | | 16 |
| 40 | organic | 0.5 | 0.77 | 14.0 | 383 |
| 40 | organic | 2.0 | 0.86 | 14.5 | 391 |
| 40 | organic | 3.0 | 0.64 | 14.1 | a |
| 40 | organic | 4.0 | 0.84 | 14.5 | 391 |
| 40 | aqueous | 0.5 | | | 12 |
| 40 | aqueous | 2.0 | | | 18 |
| 40 | aqueous | 4.0 | | | 20 |
| 60 | organic | 0.5 | nil | 13.4 | 303 |
| 60 | organic | 2.0 | nil | 11.8 | 322 |
| 60 | organic | 3.0 | nil | 11.0 | a |
| 60 | organic | 4.0 | nil | 12.2 | 322 |
| 60 | aqueous | 0.5 | | | 26 |
| 60 | aqueous | 2.0 | | | 49 |
| 60 | aqueous | 4.0 | | | 58 |
| 85 | organic | 0.5 | nil | 0.6 | 290 |
| 85 | aqueous | 0.5 | | | 91 | a Sample not analyzed.

Various modifications and variations of this invention will be obvious to a worker skilled in the art and it is to be understood that such modifications and variations are to be included within the purview of this application and the spirit and scope of the appended claims.

We claim:

1. A process for selectively removing at least about 65 percent of alkyl substituted phosphine of the formula

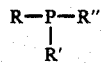

wherein R is an alkyl radical, R' is an alkyl or aryl radical and R" is an aryl radical from an organic liquid containing alkyl substituted phosphine of said formula and triarylphosphine while removing only about 15 percent or less of said triarylphosphine from said organic liquid, said process consisting of the steps of
(1) mixing said organic liquid with an aqueous solution of about 40 to about 60 percent by weight phosphoric acid,
(2) allowing the mixture to settle into two distinct liquid phases, and
(3) separating the aqueous-acidic phase which contains the protonated reaction products of said phosphines with said phosphoric acid from the non-aqueous organic phase resulting from said steps (1) and (2); and
(4) washing said non-aqueous organic phase of step (3) with an aqueous alkaline solution and then with water;
wherein the volume ratio of said aqueous phosphoric acid solution employed to the volume of said organic liquid employed is at least about 0.1 to 1, and wherein said organic liquid is a distillate of a rhodium complex catalyst containing hydroformylation medium or derivative of said distillate containing alkyl substituted phosphine of said formula and triarylphosphine, the remainder of said distillate consisting essentially of high boiling aldehyde condensation by-products.

2. A process as defined in claim 1, wherein the triarylphosphine is triphenylphosphine.

3. A process as defined in claim 2, wherein the alkyl substituted phosphine is selected from the group consisting of ethyldiphenylphosphine, propyldiphenylphosphine and butyldiphenylphosphine.

4. A process as defined in claim 3, wherein the alkyl substituted phosphine is propyldiphenylphosphine.

5. A process as defined in claim 4, wherein the phosphoric acid is employed in the form of an aqueous solution of about 60 percent by weight phosphoric acid.

6. A process as defined in claim 4, wherein the phosphoric acid is employed in the form of an aqueous solution of about 40 percent by weight phosphoric acid.

7. A process as defined in claim 1, wherein said triarylphosphine is triphenylphosphine and wherein said alkyl substituted phosphine is propyldiphenylphosphine.

8. A process as defined in claim 7, wherein about equal volumes of said aqueous phosphoric acid solution and said organic liquid are employed.

* * * * *